United States Patent
Crawford et al.

(10) Patent No.: US 9,351,881 B2
(45) Date of Patent: *May 31, 2016

(54) RETRACTABLE EARPLUG APPARATUS FOR AN EYEWEAR ASSEMBLY

(71) Applicant: ReadyMax, Inc., Elk Grove, CA (US)

(72) Inventors: Brent Crawford, Elk Grove, CA (US); Bill E. Brauner, Angels Camp, CA (US); Brad Nemeth, Oak Ridge, TN (US); Jeff Chen, Apia, AS (US); Robin Liu, Apia, AS (US)

(73) Assignee: ReadyMax, Inc., Elk Grove, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/323,906

(22) Filed: Jul. 3, 2014

(65) Prior Publication Data

US 2015/0000016 A1    Jan. 1, 2015

Related U.S. Application Data

(63) Continuation-in-part of application No. 12/908,802, filed on Oct. 20, 2010, now Pat. No. 8,794,758.

(60) Provisional application No. 61/972,881, filed on Mar. 31, 2014, provisional application No. 61/254,149, filed on Oct. 22, 2009.

(51) Int. Cl.
*G02C 1/00* (2006.01)
*A61F 11/08* (2006.01)
(Continued)

(52) U.S. Cl.
CPC ................. *A61F 11/08* (2013.01); *A61F 9/029* (2013.01); *A61F 11/06* (2013.01); *A61F 11/12* (2013.01); *G02C 5/143* (2013.01); *G02C 11/00* (2013.01); *G02C 11/06* (2013.01)

(58) Field of Classification Search
CPC .......... G02C 5/143; G02C 11/00; G02C 11/06
USPC ........................................................ 351/158
See application file for complete search history.

(56) References Cited

U.S. PATENT DOCUMENTS 2,501,107 A    3/1950    Volkmann
3,384,903 A    3/1968    Malcom, Jr.
(Continued)

FOREIGN PATENT DOCUMENTS

KR    2020120007775    5/2011

OTHER PUBLICATIONS

International Search Report dated Apr. 22, 2009 from International Application No. PCT/US2009/033242.

(Continued)

*Primary Examiner* — Huy K Mai
(74) *Attorney, Agent, or Firm* — Beyer Law Group LLP

(57) ABSTRACT

An eyewear temple arm mounted to an eyewear device, wherein a distal portion of the elongated body member defines a parking structure. A distal edge portion of the structure defines an opening into a cavity thereof which is formed and dimensioned for free sliding, peripheral receipt of at least the proximal portion of a functional element therein between an operational condition and a parked condition. A cover member is configured to cooperate with the parking structure for movement between an opened condition and a closed condition. In the opened condition, the functional element can be moved to the operational condition, while in the closed condition, the cover member extends over the parking structure opening to substantially enclose at least the distal portion of the functional element therein.

15 Claims, 17 Drawing Sheets

(51) Int. Cl.
*A61F 11/06* (2006.01)
*G02C 11/06* (2006.01)
*A61F 9/02* (2006.01)
*A61F 11/12* (2006.01)
*G02C 5/14* (2006.01)
*G02C 11/00* (2006.01)

(56) References Cited

U.S. PATENT DOCUMENTS

| | | | |
|---|---|---|---|
| 3,663,099 A * | 5/1972 | Saffir | 351/158 |
| 3,943,925 A | 3/1976 | Leight | |
| 4,901,355 A | 2/1990 | Moore | |
| RE35,051 E | 10/1995 | Moore | |
| 5,475,449 A | 12/1995 | Pyle | |
| 5,581,821 A | 12/1996 | Nakano | |
| 5,703,670 A | 12/1997 | Callard | |
| 5,715,323 A | 2/1998 | Walker | |
| 5,781,272 A | 7/1998 | Bright et al. | |
| 6,067,664 A | 5/2000 | Cortes | |
| 6,074,060 A | 6/2000 | Bruce | |
| 6,082,855 A | 7/2000 | Fleming | |
| 6,176,576 B1 | 1/2001 | Green et al. | |
| 6,340,227 B1 | 1/2002 | Solberg et al. | |
| 6,565,208 B1 | 5/2003 | Lee | |
| 6,690,807 B1 | 2/2004 | Meyer | |
| 6,905,206 B2 | 6/2005 | Skuro | |
| 7,150,526 B2 | 12/2006 | Jannard et al. | |
| 7,344,243 B2 | 3/2008 | Skuro | |
| D587,679 S | 3/2009 | Komiyama | |
| D593,067 S | 5/2009 | Millora et al. | |
| 7,810,750 B2 | 10/2010 | Abreu | |
| D666,287 S | 8/2012 | Quinlan | |
| 8,378,924 B2 | 2/2013 | Jacobsen et al. | |
| 8,794,758 B2 * | 8/2014 | Brauner et al. | 351/123 |
| 2002/0098877 A1 | 7/2002 | Glezerman | |
| 2003/0079935 A1 | 5/2003 | Weise | |
| 2007/0229755 A1 | 10/2007 | Duane | |
| 2007/0248238 A1 | 10/2007 | Abreu | |
| 2008/0143954 A1 | 6/2008 | Abreu | |
| 2010/0302501 A1 * | 12/2010 | Hansen | 351/158 |
| 2010/0319714 A1 | 12/2010 | Oshima et al. | |
| 2011/0051982 A1 | 3/2011 | Abreu | |
| 2011/0094007 A1 | 4/2011 | Brauner et al. | |

OTHER PUBLICATIONS

Written Opinion dated Apr. 22, 2009 from International Application No. PCT/US2009/033242.
U.S. Office Action dated Mar. 26, 2013 from U.S. Appl. No. 12/908,802.
U.S. Final Office Action dated Oct. 22, 2013 from U.S. Appl. No. 12/908,802.
Notice of Allowance dated Mar. 20, 2014 from U.S. Appl. No. 12/908,802.
International Search Report dated Jun. 30, 2015 from International Application No. PCT/US2015/022964.
Written Opinion dated Jun. 30, 2015 from International Application No. PCT US2015/022964.

* cited by examiner

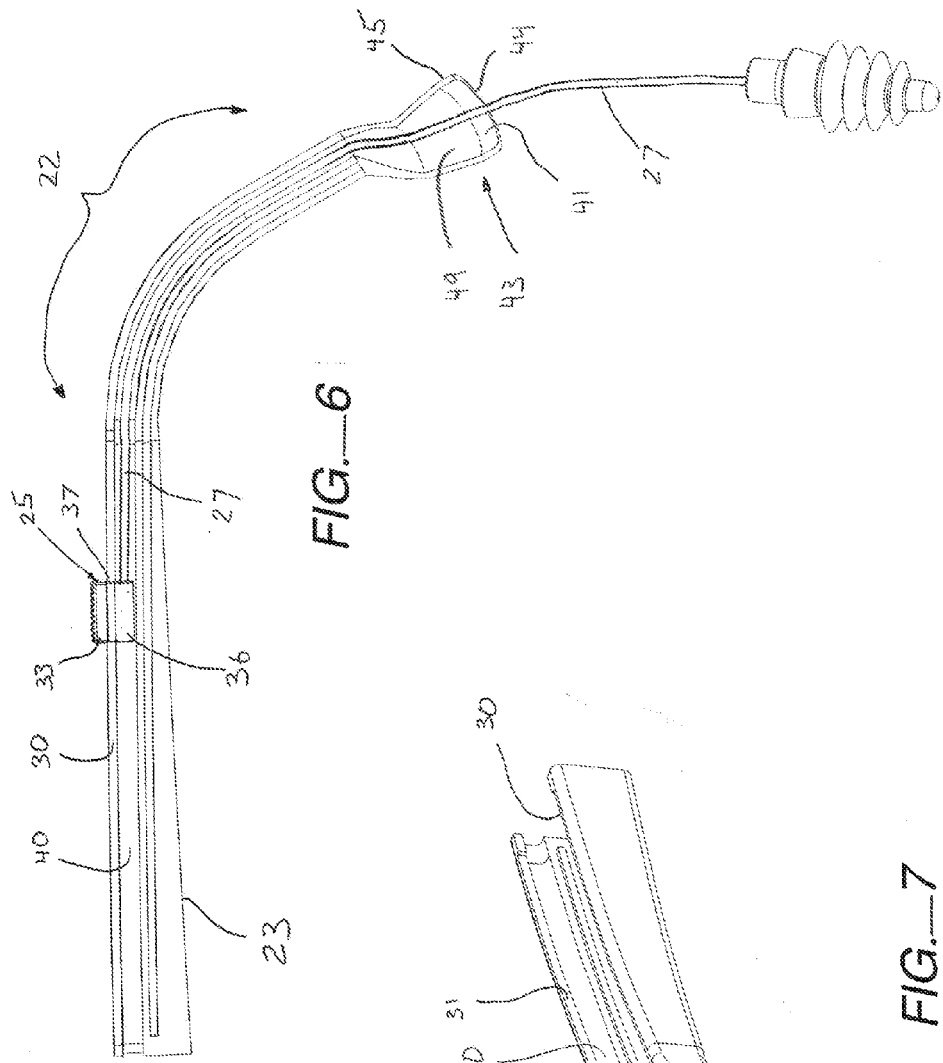
FIG._6
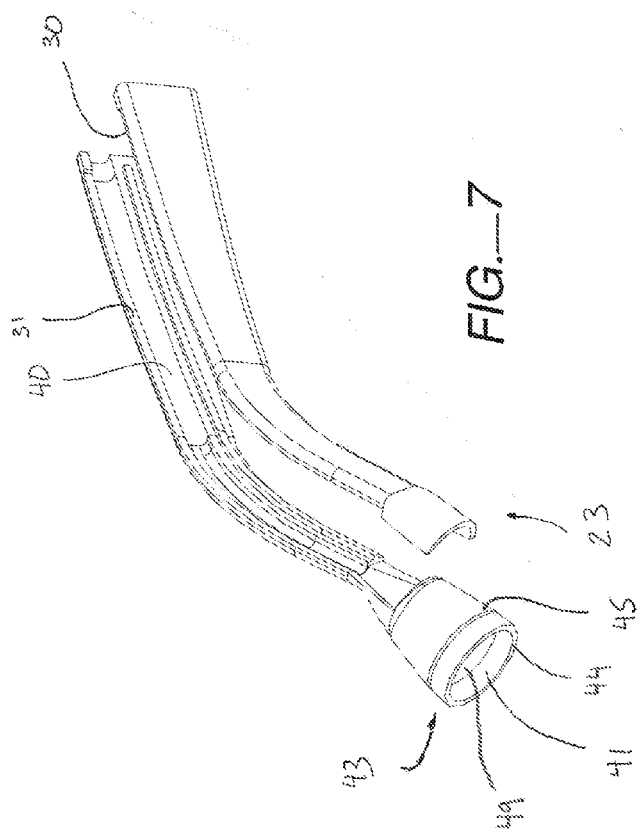
FIG._7

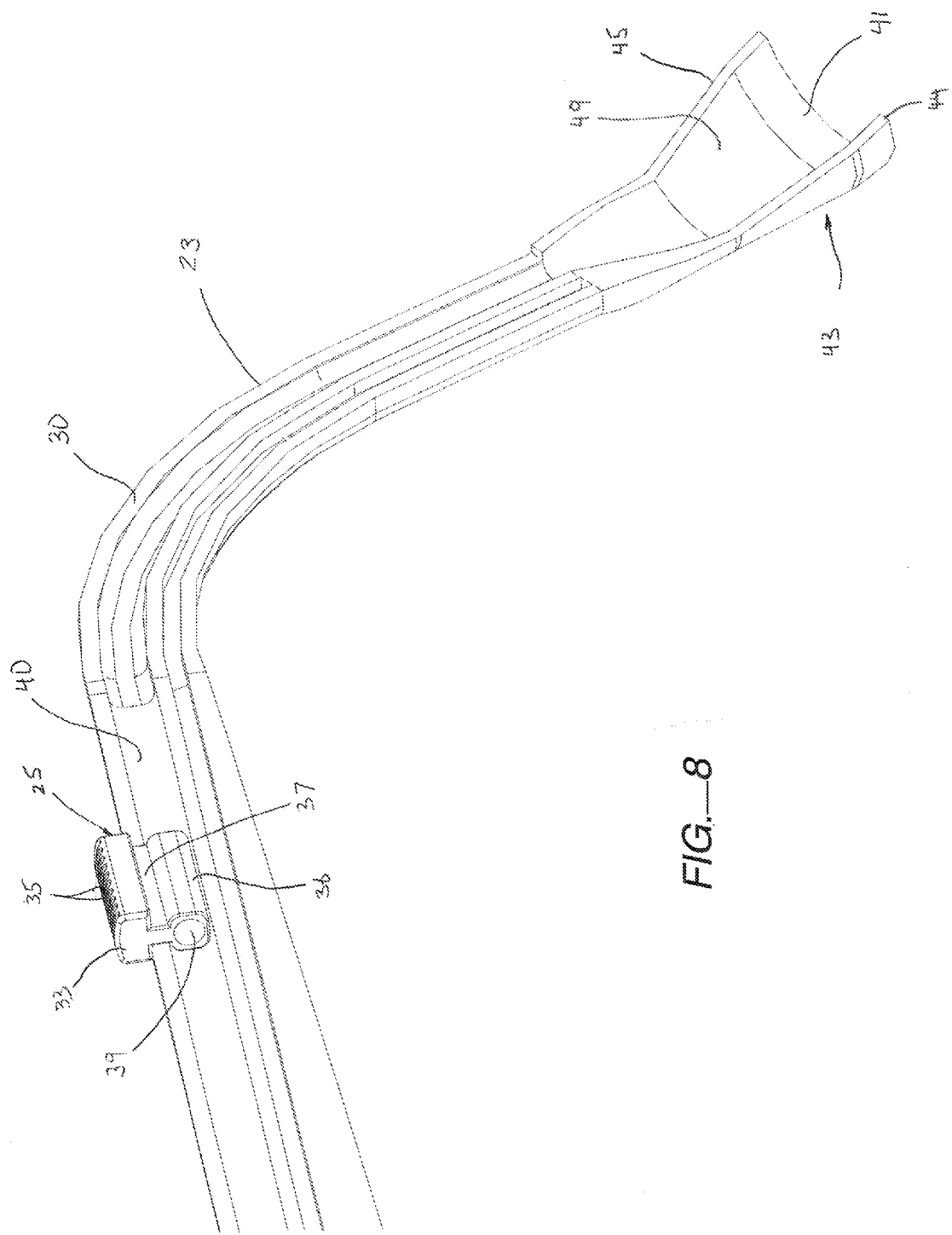

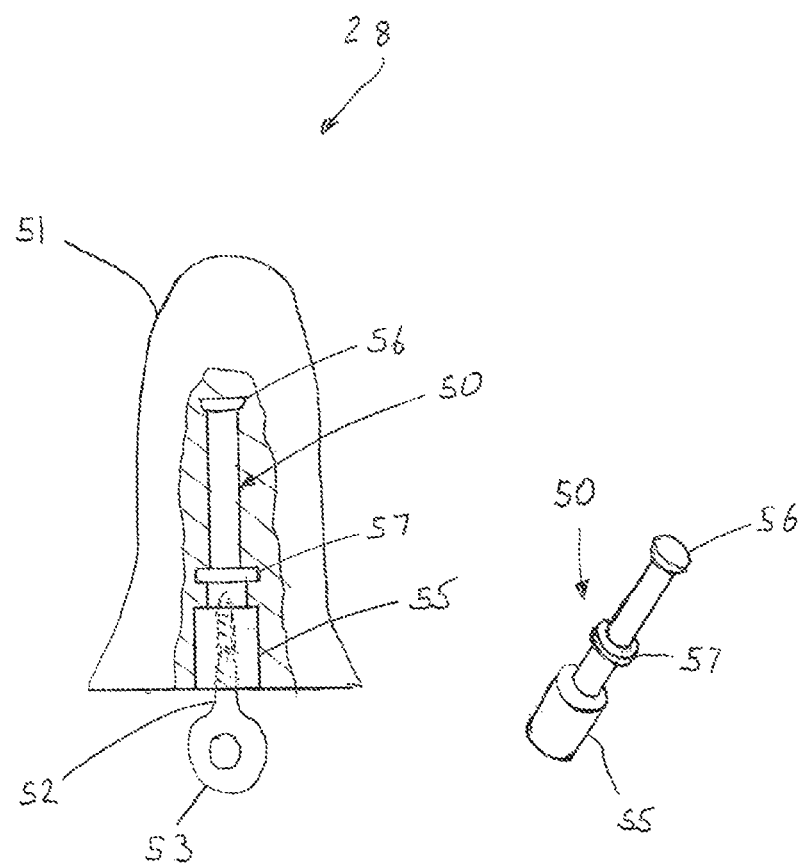

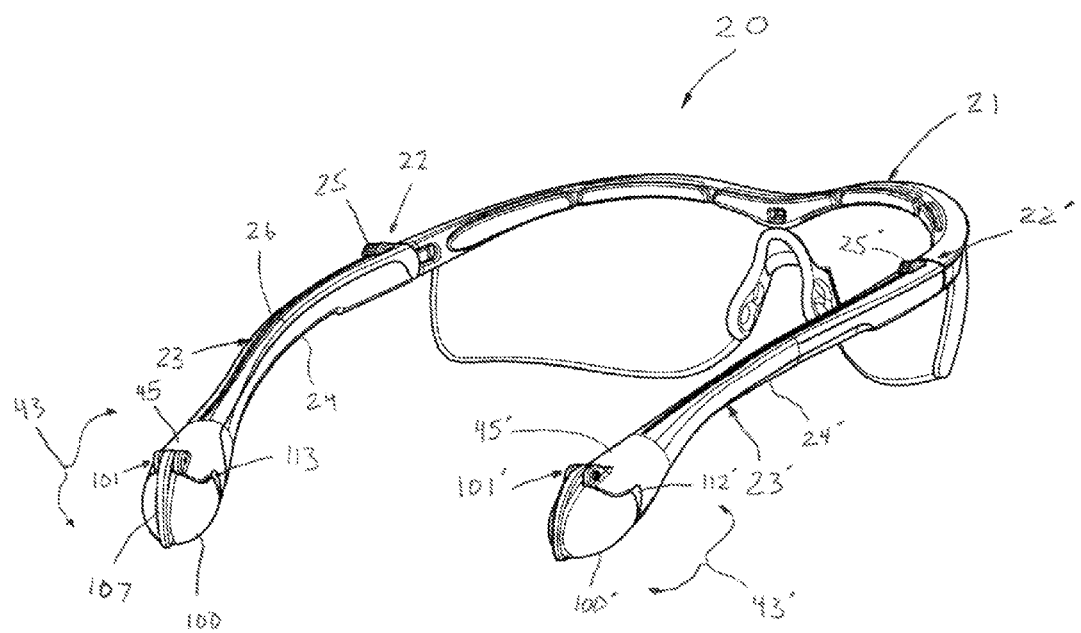
FIG._11
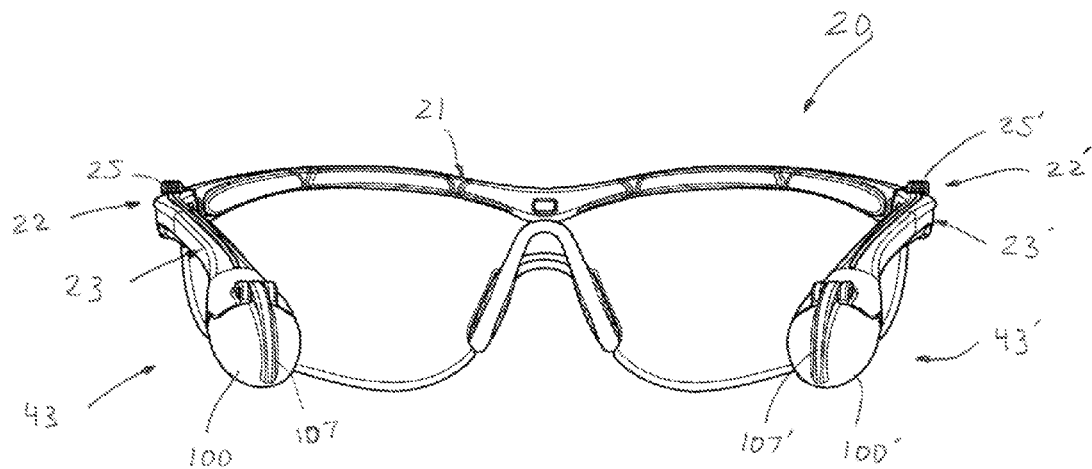
FIG._12

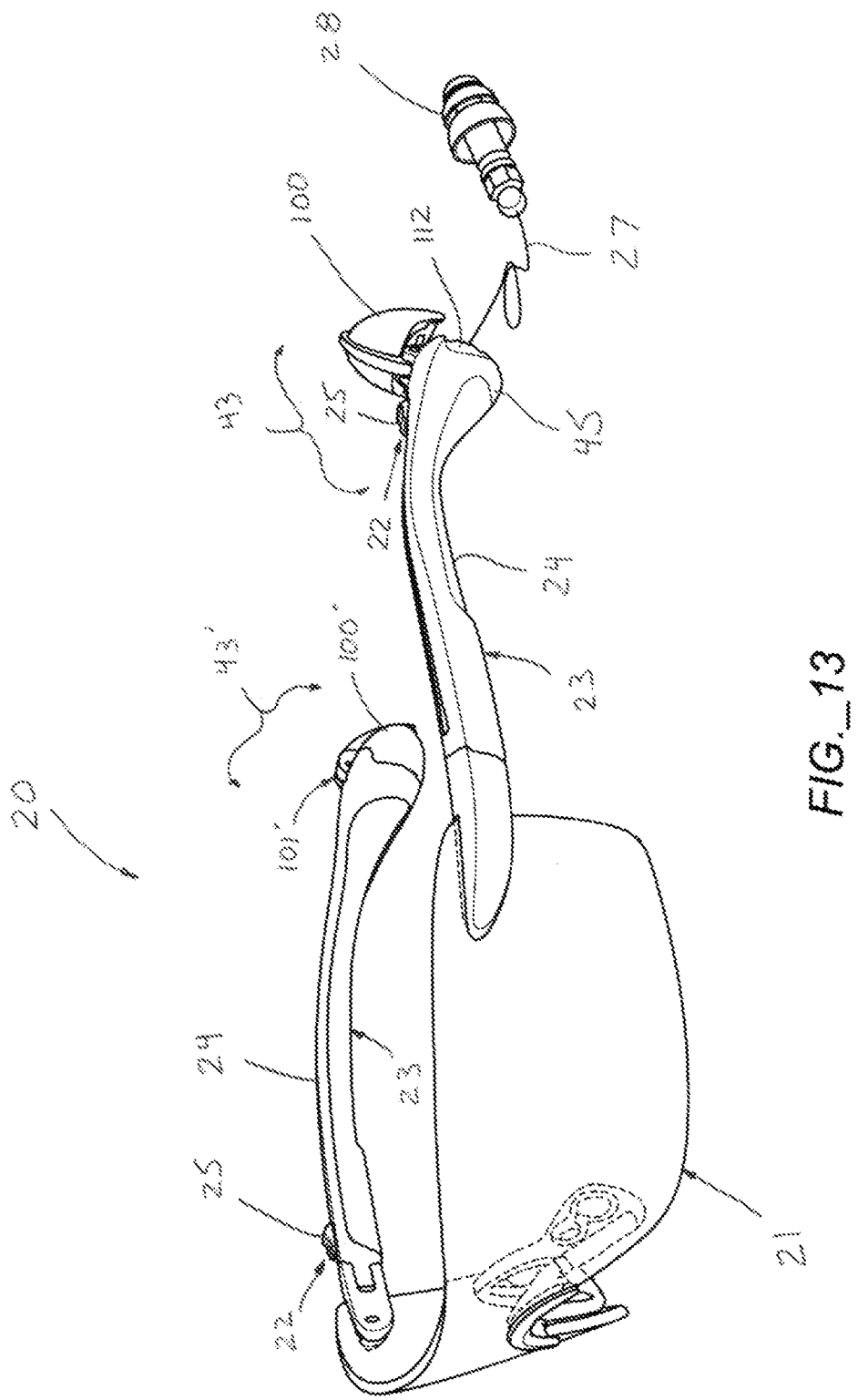
FIG._13

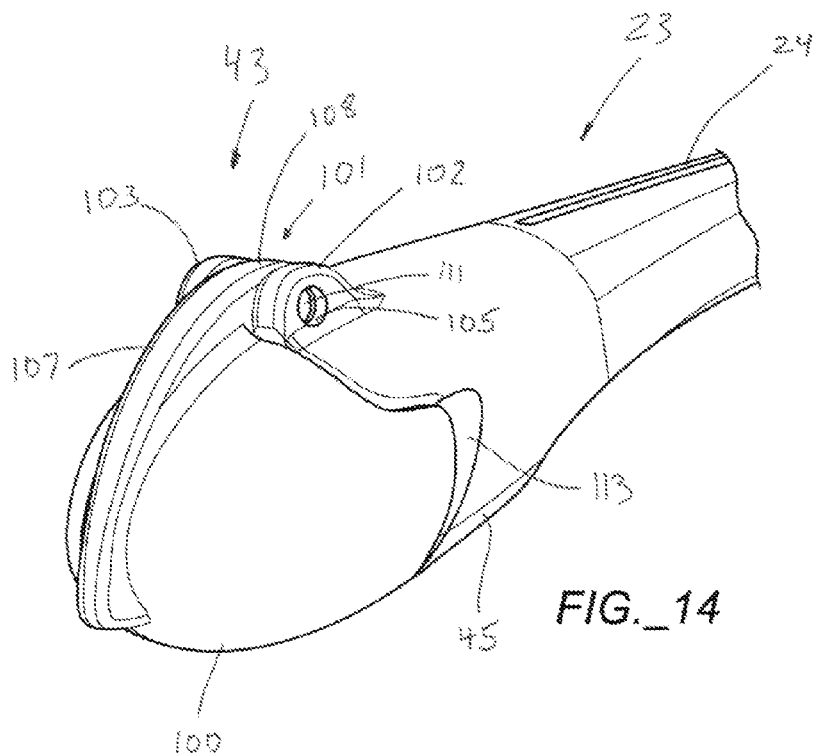
FIG._14
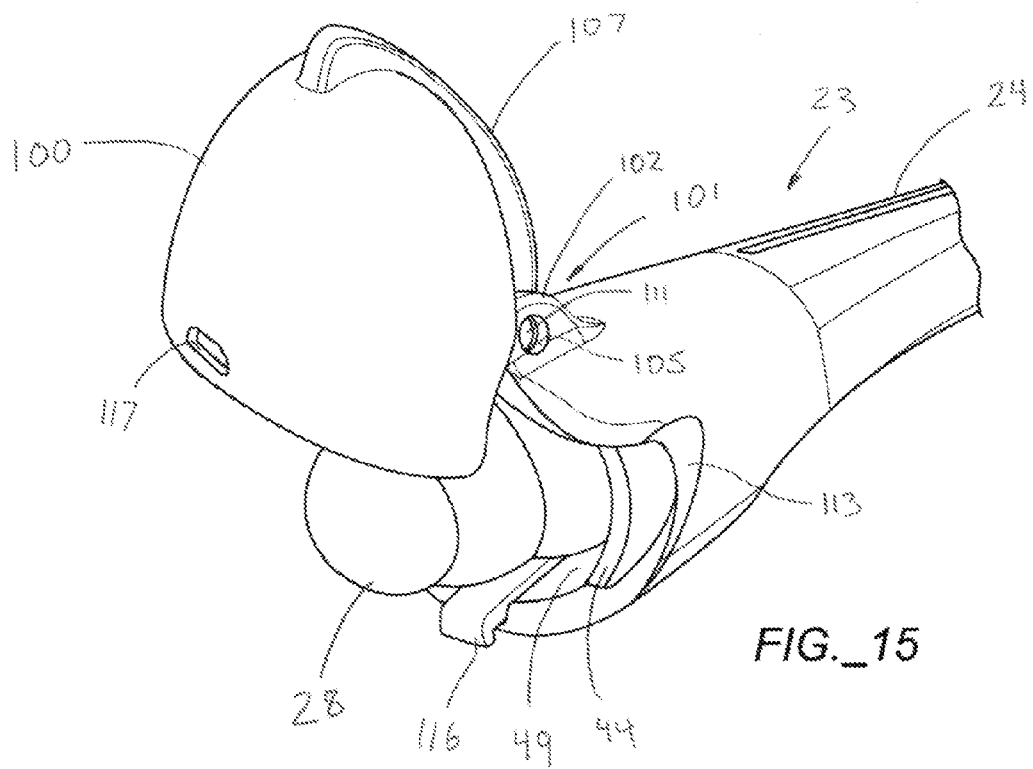
FIG._15

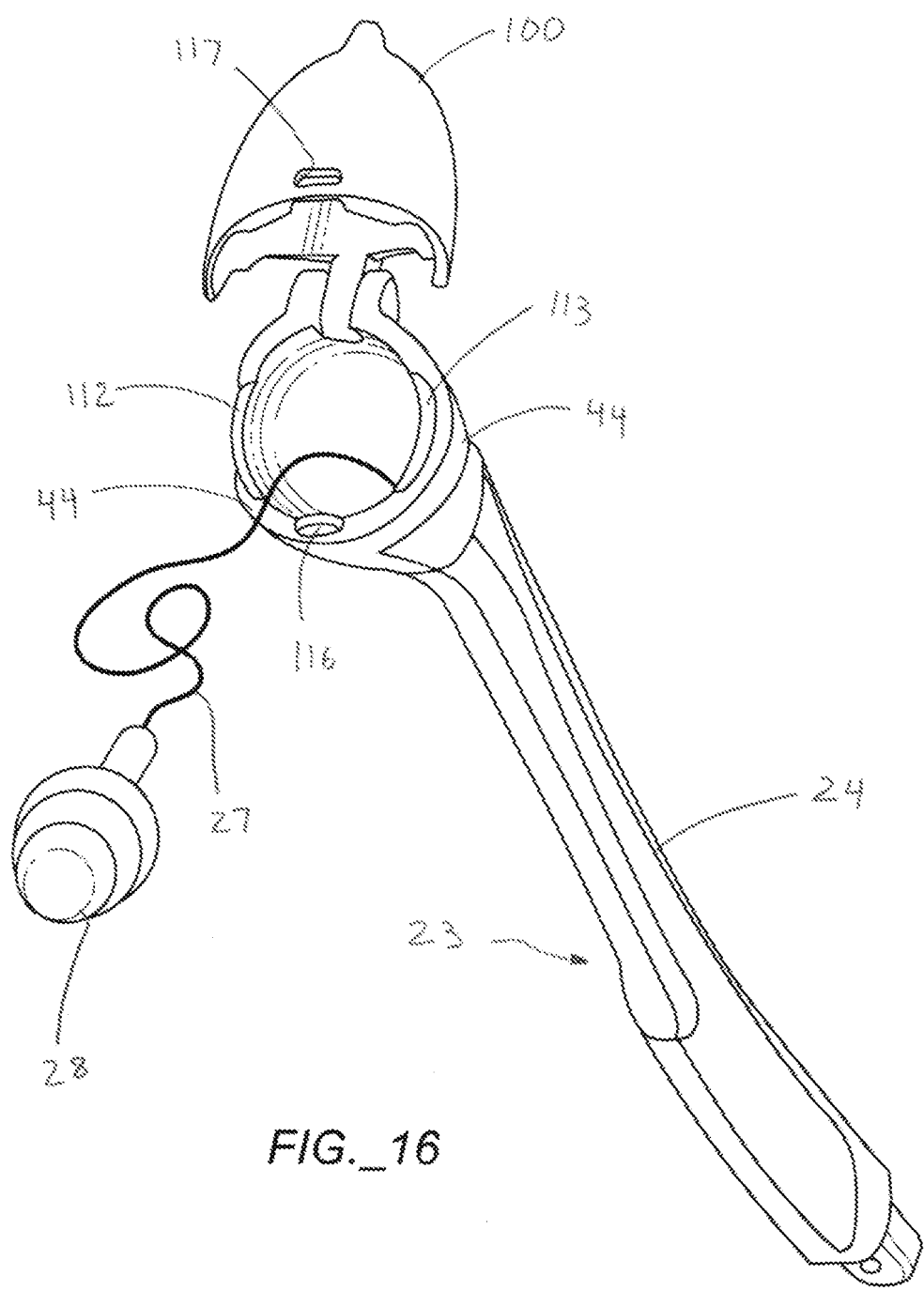
FIG._16

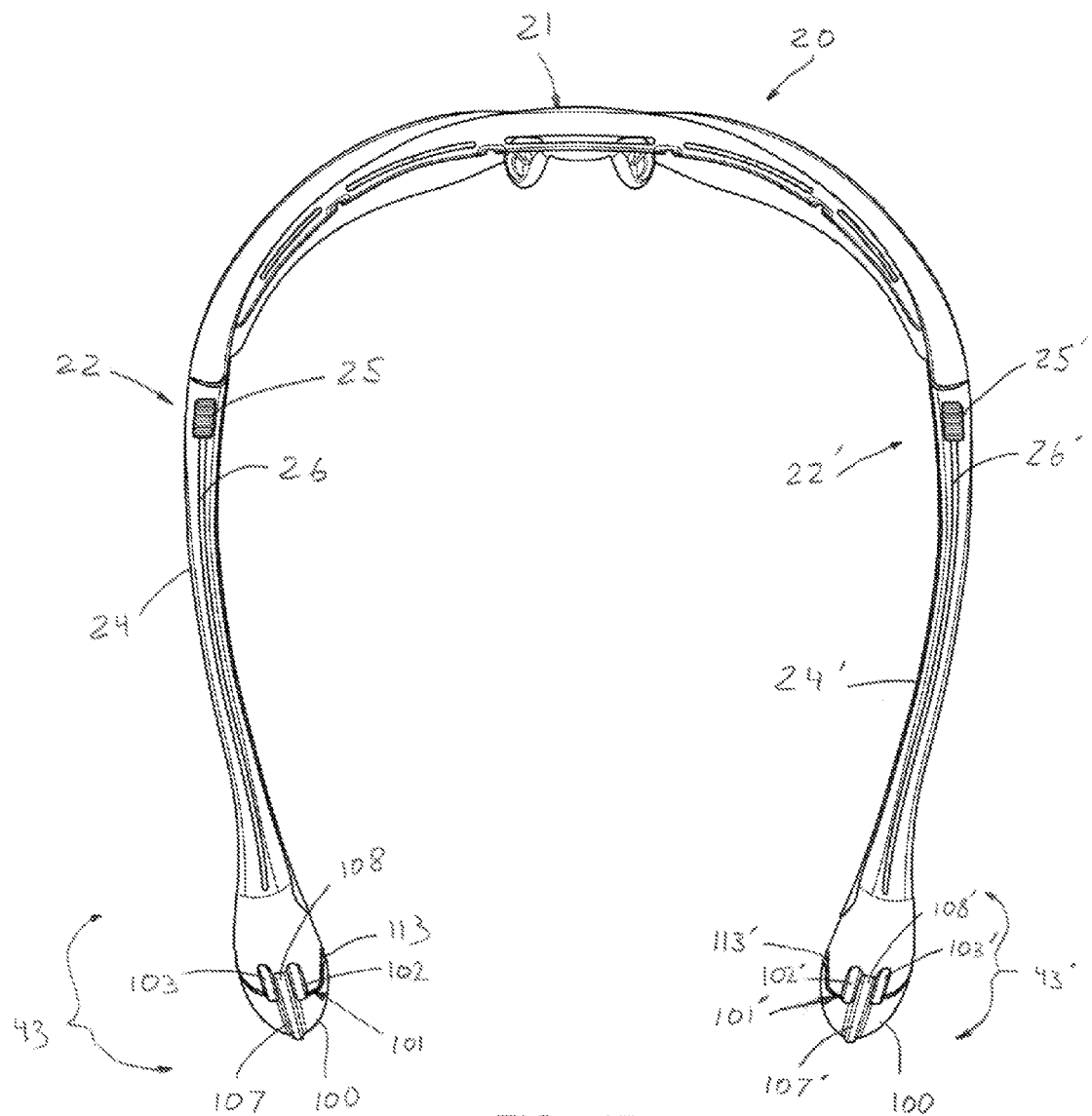
FIG._17

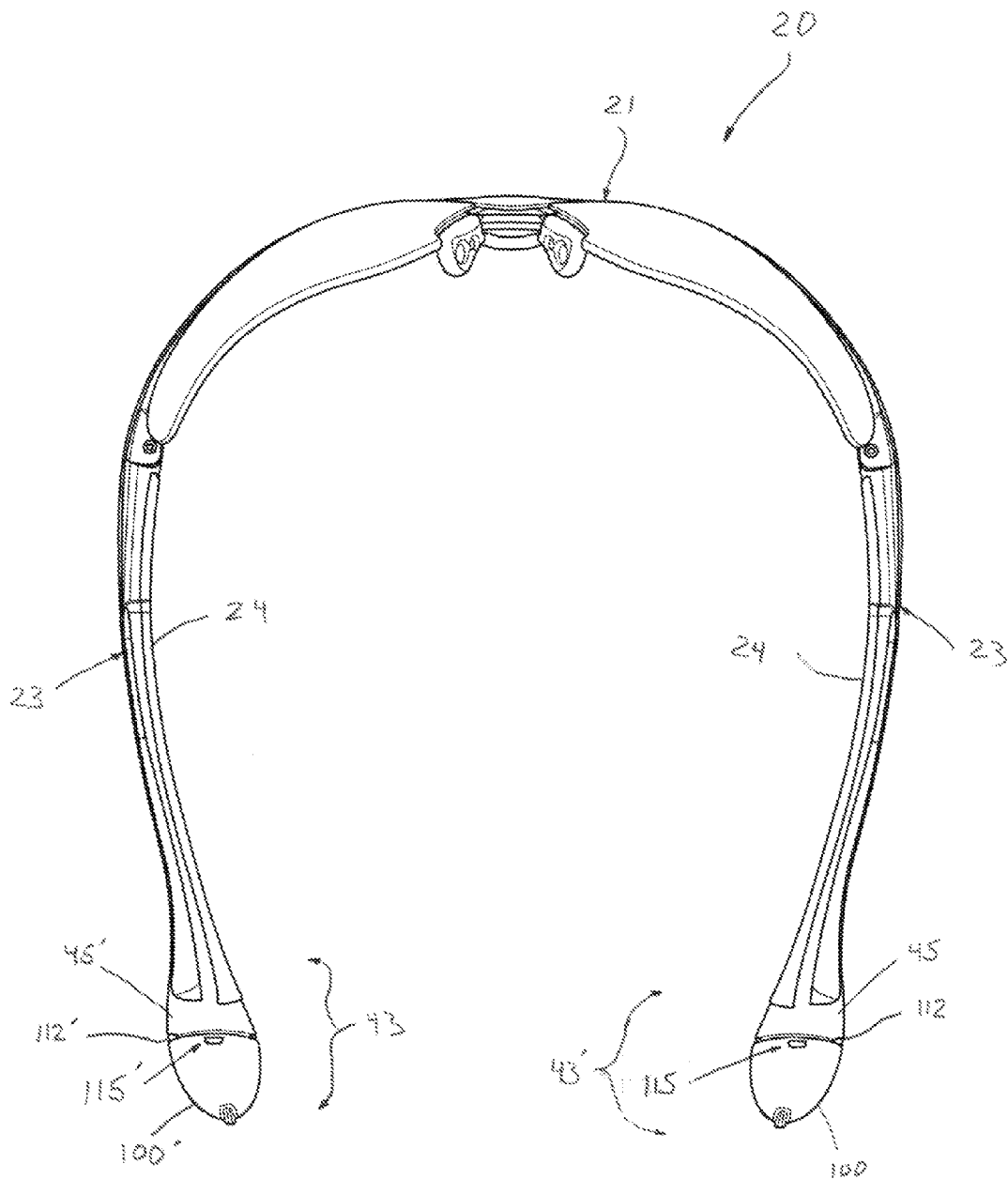
FIG._18

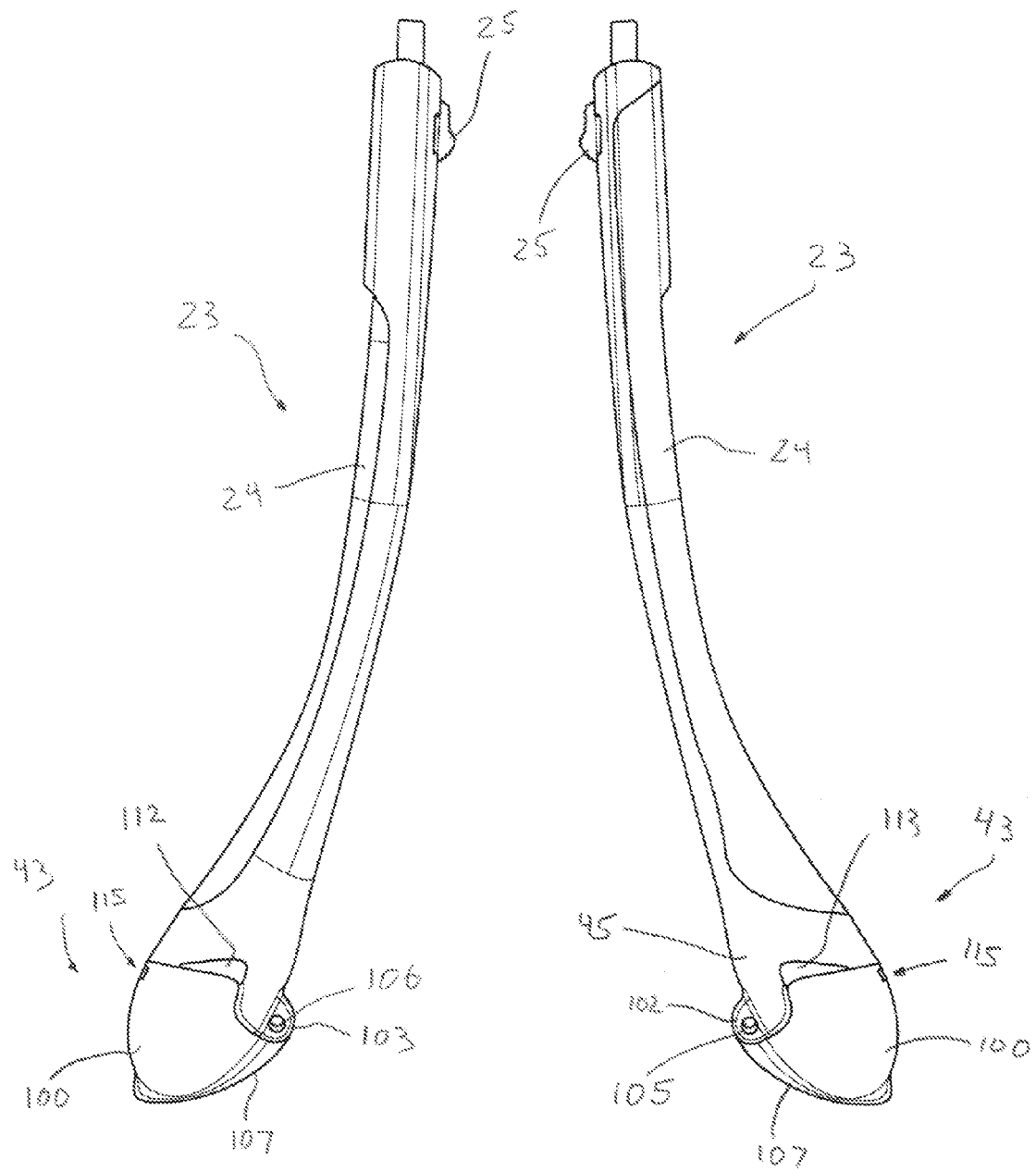
FIG._19  FIG._20

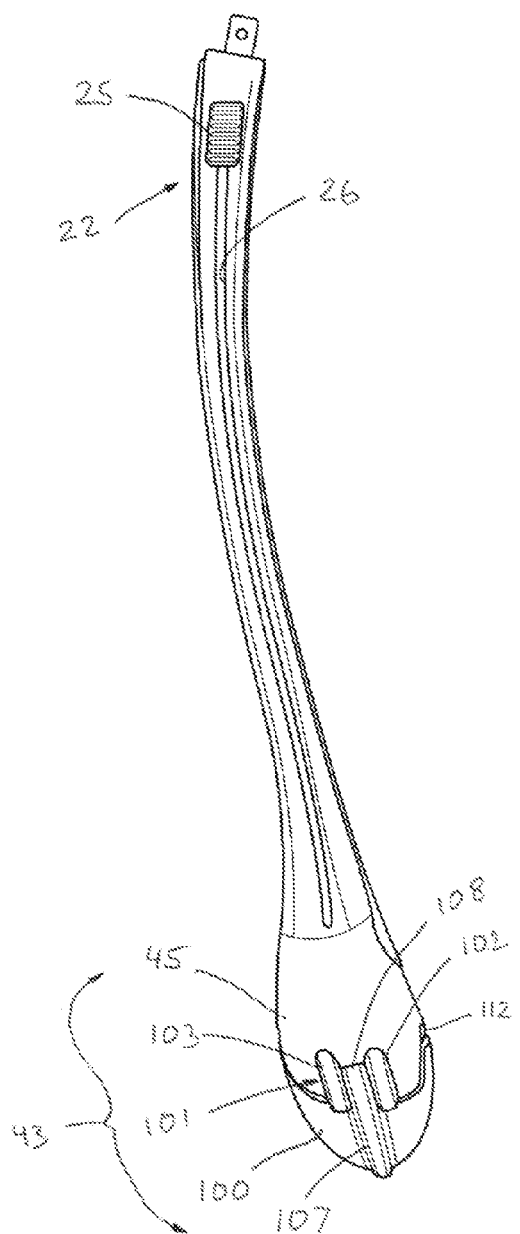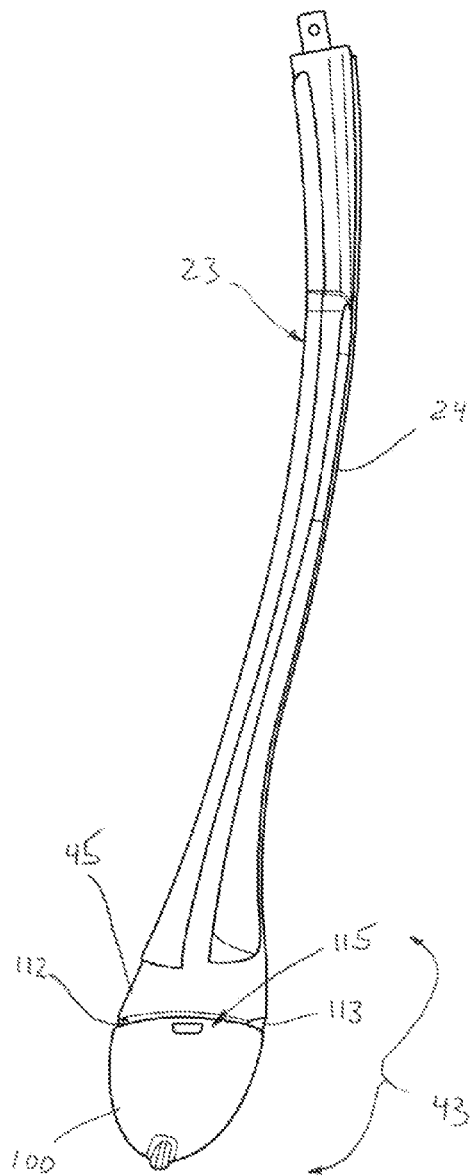
FIG._21  FIG._22

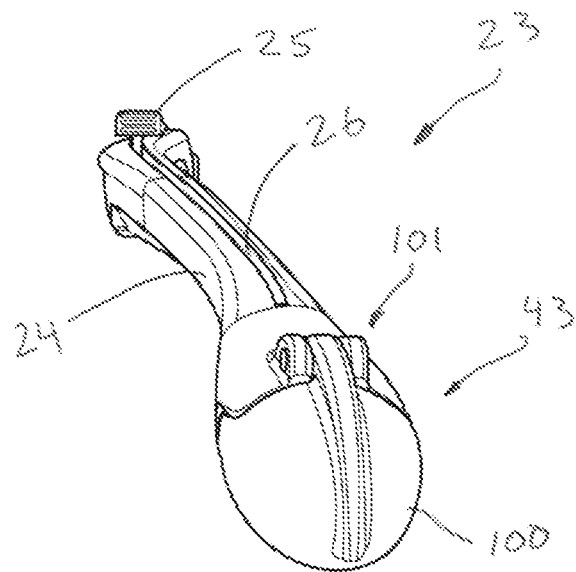
FIG._23
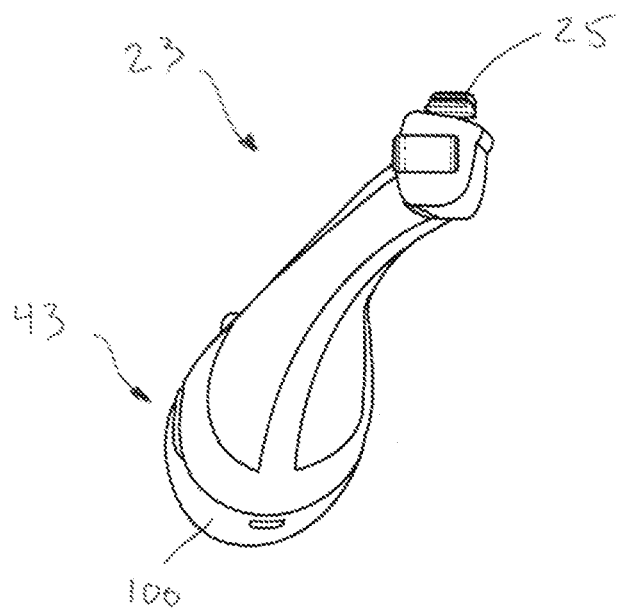
FIG._24

RETRACTABLE EARPLUG APPARATUS FOR AN EYEWEAR ASSEMBLY

RELATED APPLICATIONS

This application claims priority under 35 U.S.C. §119(e) to U.S. Provisional Patent Application No. 61/972,881, filed Mar. 31, 2014, entitled "RETRACTABLE EARPLUG ASSEMBLY FOR AN EYEWEAR ASSEMBLY", naming Crawford et al. as inventors, and further is a continuation-in-part of U.S. application Ser. No. 12/908,802, filed Oct. 20, 2010, and entitled "RETRACTABLE EARPLUG ASSEMBLY FOR AN EYEWEAR ASSEMBLY AND A VEST ASSEMBLY", naming Brauner et al. as inventors, and which in turn claims priority under 35 U.S.C. §119(e) from U.S. Provisional Application No. 61/254,149, filed Oct. 22, 2009, entitled "RETRACTABLE EARPLUG ASSEMBLY FOR AN EYEWEAR ASSEMBLY AND A VEST ASSEMBLY", naming Brauner et al. as inventors, and all of which are incorporated herein by reference in their entirety and for all purposes.

FIELD OF THE INVENTION

The present invention relates to earplug devices, and more particularly, relates to retractable tether mounted earplug assemblies retrofitted to eyewear.

BACKGROUND OF THE INVENTION

It is well known that repeated or prolonged exposure to insalubrious sounds of sufficiently high sound pressure level (SPL) may cause temporary or permanent hearing loss. This is never more apparent than at building construction sites where jackhammers, drilling, and hammering are sometimes heard simultaneously. Alone, each task can generate a significant sound level, but two or more tasks performed simultaneously can be very detrimental to those close to either event.

Fortunately, earplugs and ear protection devices have been developed that prevent harm to the eardrum and allow individuals to endure extended time in such environments. More recently, high fidelity earplugs have been developed that can be tuned to isolate the ear from certain ranges of high or low frequencies.

While the vast majority of construction workers apply some form of ear protection voluntarily, such ear protection is often mandated by state law or by the construction company itself. Typically, construction workers merely place such ear protection in their pockets or other retrievable region, during nonuse, pulling them out for use when necessary. Such small earplugs, however, are easily lost or misplaced since they often only measure less than an inch in length, Accordingly, there is a need for various apparel devices that are capable of supporting retractable mounting earplugs.

SUMMARY OF THE INVENTION

The present invention provides an eyewear temple arm apparatus for an eyewear device configured to support a functional element having a proximal portion and a distal portion. The temple arm apparatus includes an elongated body member having a proximal portion configured to mount to the eyewear device. An opposite distal portion of the elongated body member defines a parking structure having a distal edge portion that further defines an opening into a cavity thereof. The cavity is formed and dimensioned for free sliding, peripheral receipt of at least the proximal portion of the functional element therein between an operational condition and a parked condition. The temple arm apparatus further includes a cover member configured to cooperate with the parking structure for movement between an opened condition and a closed condition. In the opened condition, the functional element can be moved to the operational condition, while in the closed condition, the cover member extends over the parking structure opening to substantially enclose at least the distal portion of the functional element therein.

Accordingly, an eyewear assembly is provided having retractable functional elements, such as an earplug or clip device, integrally mounted to the temple arms of the eyewear. In accordance with the present invention, the functional element can be removably stored and fully enclosed within the parking structure during non-use. This is advantageous, in one example, in that usable earplugs can be integrally provided with the eyewear device for use, in the operational condition, that can easily stowed away and protected during periods of non-use, in the parked condition In one specific embodiment, the cover member hingeable moves between the opened condition and the closed condition.

In another configuration, the cover member is a generally dome-shaped shell.

In still another embodiment, temple arm apparatus further includes an elongated flexible tether having a distal portion thereof mounted to the earplug, and slideably extending through the parking structure cavity.

Yet another specific embodiment further includes a guide base slideably cooperating with the elongated body member for movement between a first position and a second position. The elongated body member defines a passageway extending longitudinally therethrough and distally terminates at the parking structure cavity. The passageway is sized and dimensioned for reciprocal sliding receipt of the tether therein as the guide base is moved between the first position and the second position.

In another aspect of the present invention, an eyewear assembly includes an eyewear device, and a pair of temple arms each having an elongated body member with a respective proximal portion thereof mounted at opposed sides of the eyewear device. Each body member includes an opposite distal portion thereof defining a respective parking structure with an opening into a substantially enclosed cavity thereof. Each cavity is formed and dimensioned for free sliding, peripheral receipt of at least a proximal portion of a respective functional element therein between an operational condition and a parked condition. The eyewear assembly further includes a cover member configured to cooperate with the parking structure for movement between an opened condition, enabling the respective functional element therein to move to the operational condition, and a closed condition, extending over the parking structure opening to substantially enclose at least the distal portion of the respective functional element therein.

In another specific embodiment, the eyewear assembly includes a pair of support mechanisms each cooperating between a respective temple arm and a respective functional element to enable movement thereof between the parked condition, parked relative to the respective temple arm, and the operational condition. In the operational condition, the functional element is positioned sufficiently away from the respective temple arm to enable operation thereof.

The support mechanism includes a respective elongated flexible tether, each cooperating with the respective temple arm for positioning between a retracted condition and an extended condition. A distal end of each respective tether is mounted to the proximal portion of each respective functional element such that when the respective tether is moved between the retracted condition and the extended condition, the respective functional element is moved between the parked condition and the operational condition.

In yet another aspect of the present invention, an eyewear temple arm apparatus is provided for an eyewear device having an elongated body member having a proximal portion configured to mount to the eyewear device. An opposite distal portion thereof defines a parking structure having an opening into a substantially enclosed cavity. An elongated flexible tether has a distal portion thereof mounted to the functional element, and the tether slideably extends through the parking structure cavity for movement of functional element between a parked condition, slideably parking the functional element at least partially within the cavity, and an operational condition, positioning the functional element sufficiently out of the parking structure to enable operation thereof. A cover member is configured to cooperate with the parking structure for movement between an opened condition, enabling the functional element therein to move to the operational condition, and a closed condition, extending over the parking structure opening wherein the parking structure and the cover member cooperate to substantially enclose the functional element.

In one embodiment, eyewear temple arm includes a guide base slideably cooperating with the elongated body member for movement between a first position and a second position. An elongated flexible tether is included having a proximal end mounted to the guide base and a distal portion thereof mounted to the functional element. The elongated body member defines a passageway extending longitudinally therethrough and distally terminating at the parking structure cavity. The passageway is sized and dimensioned for reciprocal sliding receipt of the tether therein as the guide base is moved between the first position and the second position.

In yet another embodiment, the functional element is an earplug.

BRIEF DESCRIPTION OF THE DRAWINGS

The assembly of the present invention has other objects and features of advantage which will be more readily apparent from the following description of the best mode of carrying out the invention and the appended claims, when taken in conjunction with the accompanying drawings, in which:

FIG. 6 is an enlarged side elevation view of the temple arm of FIG. 4 with one portion of the temple arm removed to expose the passageway thereof.

FIG. 7 is an exploded, top perspective view of the temple arm of FIG. 4, earplug assembly of FIG. 5, in the extended condition.

FIG. 8 is an enlarged, fragmentary, side perspective view of the temple arm of FIG. 6 with the tether device and earplug device removed.

FIG. 9 is a side elevation view, partially broken away, of an earplug device constructed in accordance with another aspect of the present invention.

FIG. 10 is a top perspective view of a central post member for the earplug device of FIG. 9.

FIG. 11 is a top perspective view of an eyewear assembly having an alternative embodiment temple arm having a garage structure with a cover member constructed in accordance with the present invention.

FIG. 12 is a rear elevation view of the eyewear assembly of FIG. 11.

FIG. 13 is a top perspective view of the eyewear assembly of FIG. 11.

FIG. 14 is an enlarged, fragmentary, top perspective view of the garage structure of the temple arm of FIG. 11, showing the cover member in a closed condition.

FIG. 15 is a fragmentary, top perspective view of the garage structure of the temple arm of FIG. 14, showing the cover member in an opened condition.

FIG. 16 is an enlarged top perspective view of the temple arm of FIG. 11, showing the cover member in the opened condition with the earplug device in an operational condition FIG. 17 is a top plan view of the eyewear assembly of FIG. 11.

FIG. 18 is a bottom plan view of the eyewear assembly of FIG. 11.

FIG. 19 is a left side elevation view of the left temple arm of eyewear assembly of FIG. 11.

FIG. 20 is a right side view of the left temple arm of FIG. 11.

FIG. 21 is a top plan view of the left temple arm of FIG. 11.

FIG. 22 is a bottom plan view of the left temple arm of FIG. 11.

FIG. 23 is a rear elevation view of the left temple arm of FIG. 11.

FIG. 24 is a front elevation view of the left temple arm of FIG. 11.

DETAILED DESCRIPTION OF THE INVENTION

Figure 1:
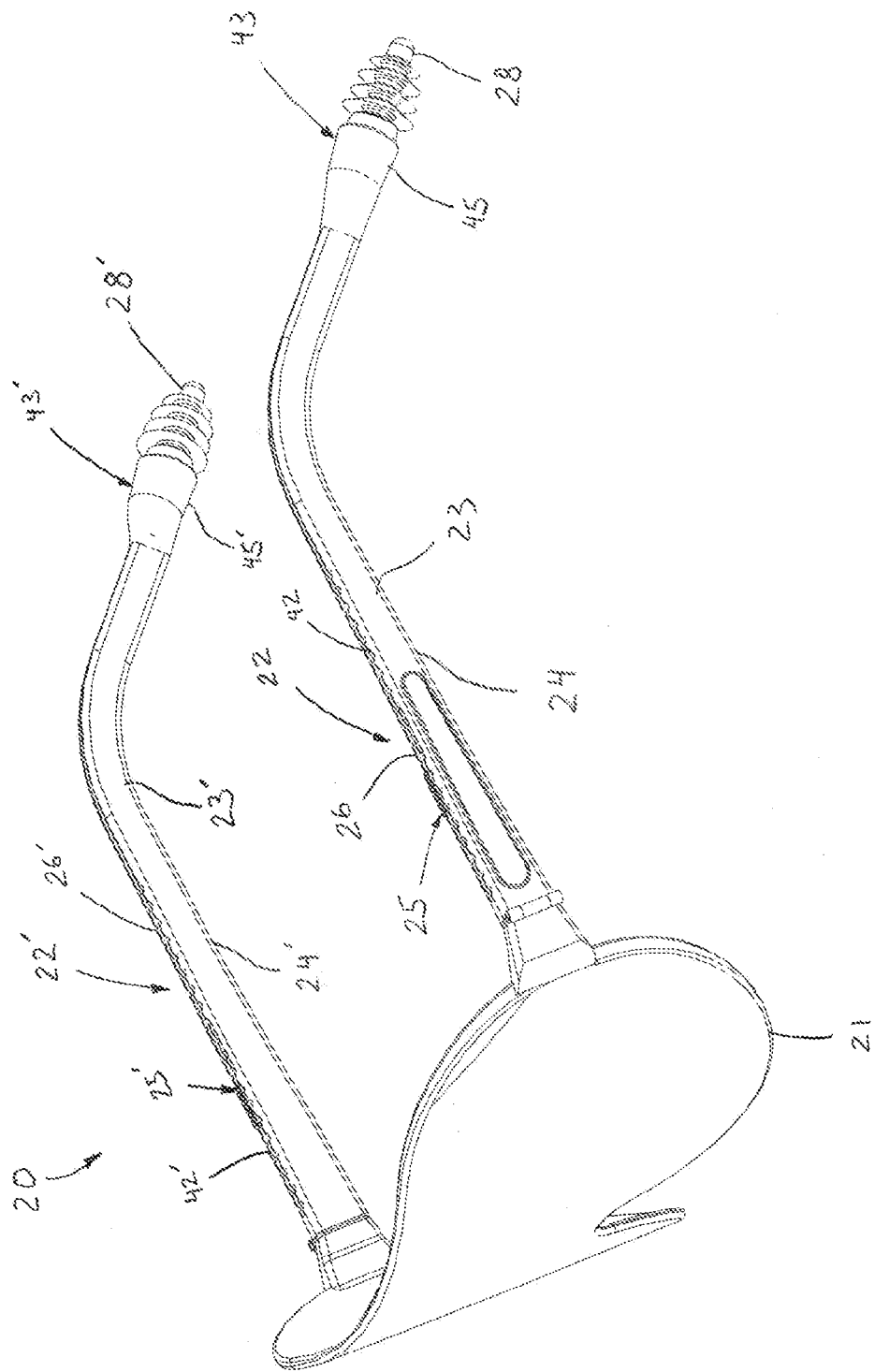
FIG. 1 is a front perspective view of an eyewear assembly incorporating a support mechanism constructed in accordance with the present invention, illustrated in a retracted condition.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

Referring now to the embodiment of FIGS. 1-8, an eyewear assembly 20 is provided, such as conventional eyeglasses, having eyewear device 21 (framed or unitary piece) that incorporates retractable support mechanisms 22, 22' in the temple arms 23, 23' of the eyewear assembly. Briefly, each support mechanism 22, 22' includes a respective guide base 25, 25' slideably mounted to a corresponding temple arm 23, 23' for selective movement between a first position (FIGS. 1 and 2) and a second position (FIGS. 4-7). More preferably, the guide base 25 configured to slideably cooperate with a guide track 26, 26' integrally formed in a respective temple arm 23, 23', for movement thereof along a fixed path in a direction generally longitudinally therealong between the first position and the second position.

Further, each support mechanism 22, 22' includes a flexible tether device 27, 27' having a proximal end mounted to the slideable guide base 25, 25' and an opposite distal end mounted to a functional 28, 28' element capable of a functional operation. Accordingly, as the slideable guide base 25, 25' is selectively moved between the first position and the second position, the respective functional element 28, 28', via corresponding tethers 27, 27', are moved between a parked condition (FIGS. 1 and 2), enabling parking and storage of the functional elements, and an operational condition (FIGS. 4-7), enabling operational use thereof.

Accordingly, an eyewear assembly 20 is provided having retractable functional elements, such as earplug devices shown in the figures for instance, integrally mounted to the temple arms of the eyewear. This is beneficial in that usable earplugs can be integrally provided with the eyewear device for use, in the operational condition, that can easily stowed away during periods of non-use, in the parked condition. When the guide base 25, 25' moves along the fixed path between the first position (FIGS. 1 and 2) and the second position (FIGS. 4-7), the tether device 27, 27' and the functional elements 28, 28' move between the parked condition (FIGS. 1 and 2) and the operational condition (FIGS. 4-7). As mentioned, in the operational condition, when the eyewear assembly 20 is being worn, the distal end of the flexible tether device 27, 27', in an extended condition, is extended sufficiently away from the corresponding temple arm to enable operational access to the corresponding functional element 28, 28'.

It will be appreciated that the functional elements 28, 28' may be essentially any tool or device that is functional in nature, and that is relatively small so that it is capable of being parked and/or stored adjacent a distal portion of the temple arm. By way of example, such a functional element may be provided by an earplug device, a clip device, and a bottle opener. For illustrative purposes, however, an earplug device is illustrated in the figures for simplicity.

Figure 2:
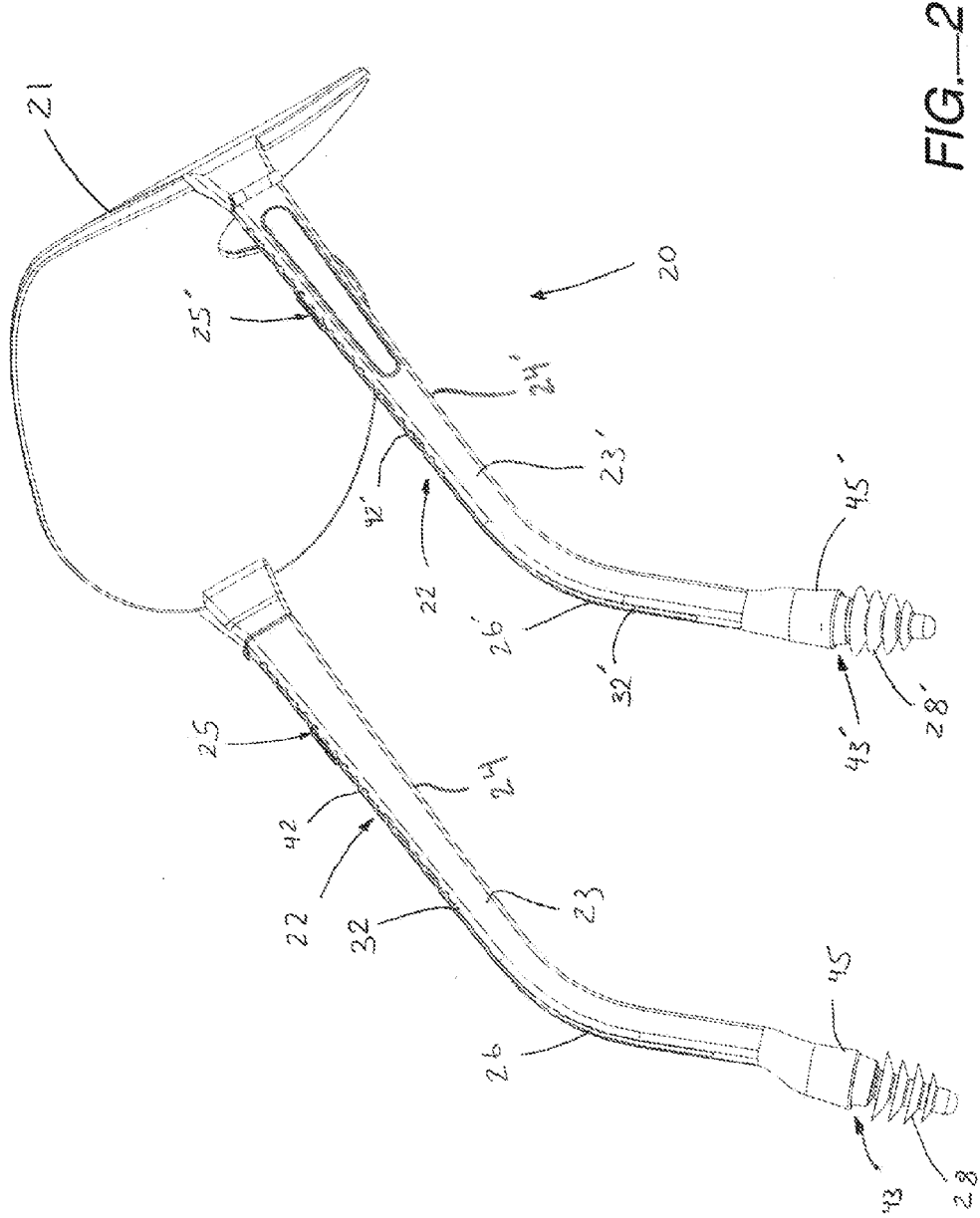
FIG. 2 is a rear perspective view of the eyewear assembly of FIG. 1.
Figure 3:
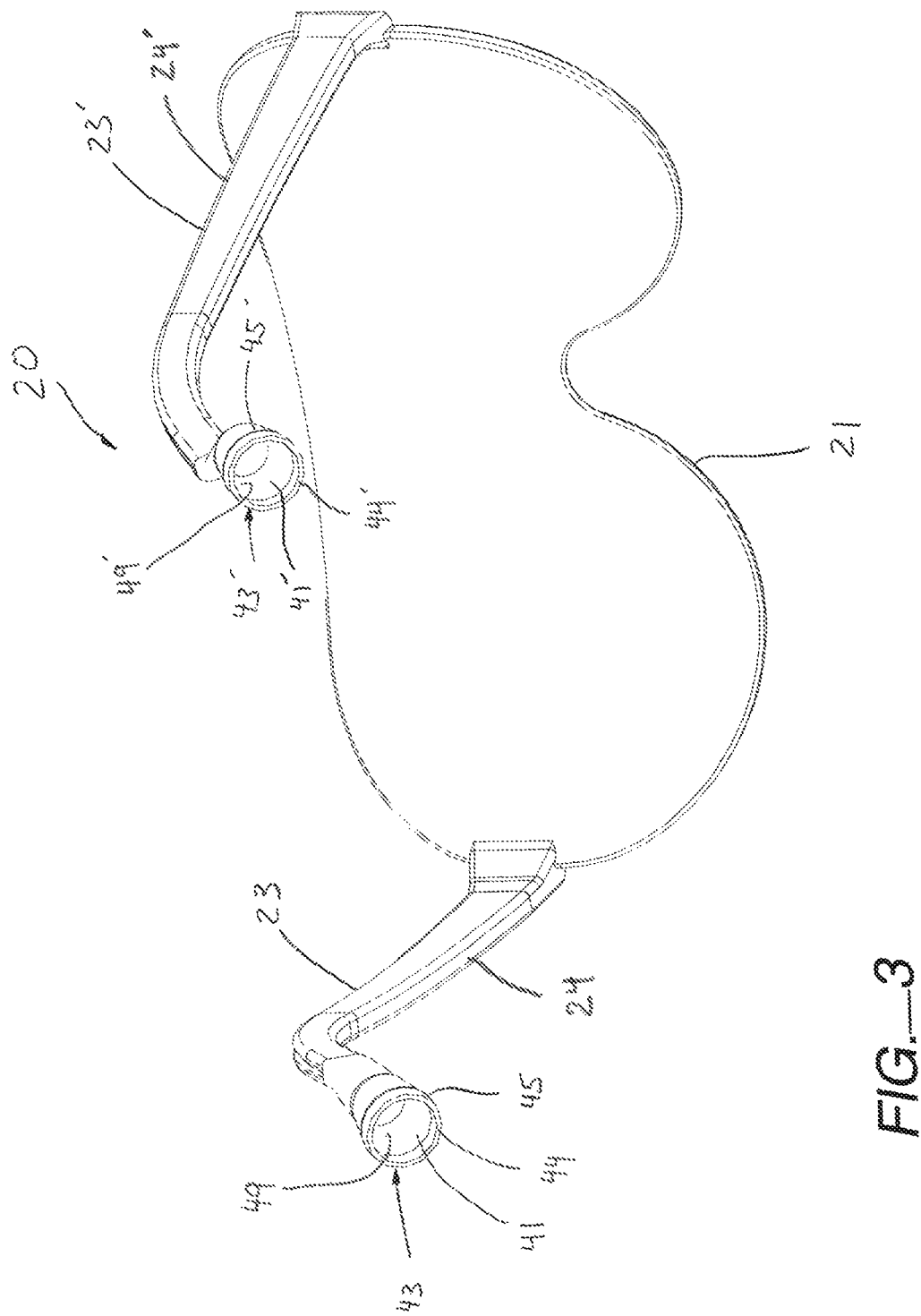
FIG. 3 is a bottom perspective view of the eyewear assembly of FIG. 1, with the earplug devices removed.
Figure 4:
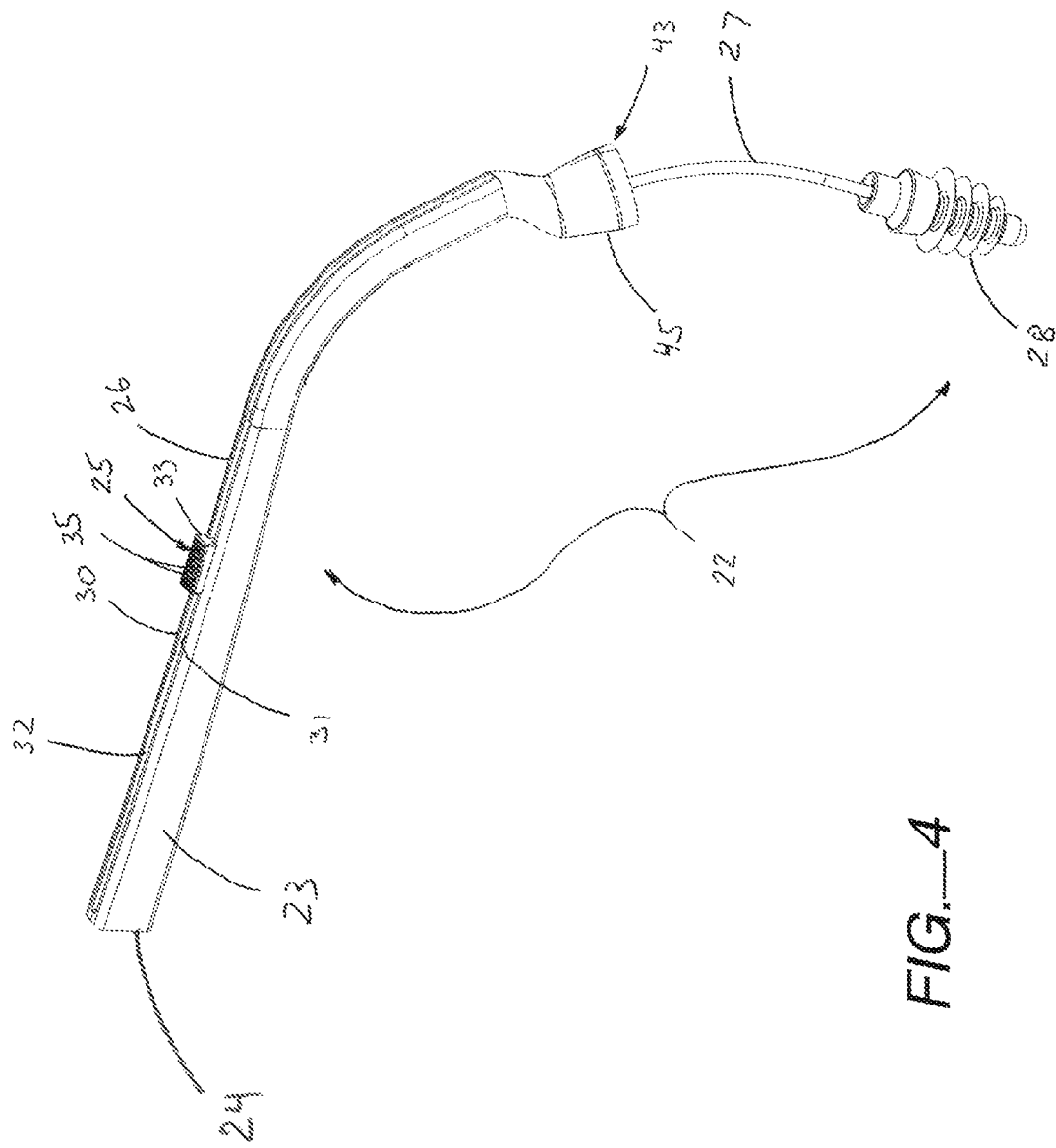
FIG. 4 is a side elevation of a temple arm of the eyewear assembly of FIG. 1, with the support mechanism in an extended condition.

In the first position, the guide base 25, 25' cooperates with the respective temple arm to position and slideably move the respective tether device 27, 27' along the fixed path, to a retracted condition, wherein the corresponding earplug device 28, 28' is drawn into, or positioned adjacent or proximate to the distal end of the temple arm 23. Accordingly, as shown in FIGS. 1 and 2, in this retracted condition, the tether device 27 does not freely hang or dangle about the eyewear to prevent entanglement. A much more organized and cleaner appearance is provided. Moreover, this position enables easy access to grip the earplug 28, 28' so that the user can manually pull the earplug device and/or tether toward the extended condition. In the extended condition, of course, the tether is extended from the distal end of the temple arm 23, 23' to enable the earplug device 28, 28' to be placed in the user's ears for use.

Referring now to FIGS. 4-8, only one temple arm 23 with the integrated support mechanism 22 will be described in detail. Briefly, the temple arm apparatus 23 includes an elongated body member 24 having a proximal end portion configured to mount to the eyewear device 21, and an opposite distal end portion thereof defining a parking structure 43 formed and dimensioned for removable receipt of the functional element 28 (e.g., earplug devices) therein.

As mentioned, the guide base 25 of the support mechanism 22 is slideably mounted to the guide track 26 that is integrally formed in the temple arm 23 for movement between the first and second positions. The guide track 26 includes a pair of thin opposed flanges 30, 31 that collectively define an elongated guide slot 32 extending substantially longitudinally along the length of the temple arm 23 between the first and second positions. The guide slot 32 is formed and dimensioned for sliding support of the guide base 25 during movement between the first and second conditions.

Briefly, each guide base 25 includes an upper slide tab portion 33 formed for selective manual manipulation of the base for positioning thereof along the slot 32. In one configuration, the tab portion 33 is substantially rectangular shaped, having a generally flat upper surface that defines a plurality of traction ridges 35 or the like to facilitate gripping manipulation thereof.

The guide base 25 further includes a generally cylindrical-shaped mounting portion 36 positioned below the upper tab portion 33. The mounting portion 36 is connected to, and spaced-apart from, the tab portion 33 by a vertically oriented support wall 37 therebetween. The transverse cross-sectional dimension of the support wall 37, as shown in FIGS. 5 and 8, is sized and formed for sliding receipt in the guide slot 32, permitting reciprocal movement of the guide base 25 therebetween.

The mounting portion 36 of the guide base 25 is formed and dimensioned for sliding receipt in a passageway 40 of the temple arm 23 that extends longitudinally therealong from the first position to the second position. Briefly, this passageway further extends adjacent to, and is in communication with, the guide slot 32. The passageway 40, however, extends to the distal end of the temple arm, via distal end opening 41, whereas the guide slot 32 is narrower in width and does not extend all the way to the distal end. To slidingly accommodate the mounting portion 36 of the guide base, a transverse cross-sectional dimension of the passageway is at least slightly larger than that of the base mounting portion.

The cylindrical mounting portion 36 is further formed to couple to the proximal end of the tether device 27, for selective manipulation of the tether device and mounted earplug between the retracted condition (FIGS. 1 and 2) and the extended condition (FIGS. 4-7), as the guide base is manipulated between the first and second positions, respectively. As best illustrated in FIGS. 6 and 8, in one embodiment, the proximal end may be simply friction fit received in a mounting channel 39 extending longitudinally through the mounting portion 36. Thus, when the guide base 25 is oriented in the first position, the tether device 27 is retracted into, and retained, in the passageway 40, toward the retracted condition. This channel 40, therefore, is not only formed and dimensioned for sliding receipt of the mounting structure therein, but also receives, protects and stores the tether device 27, when oriented in the retracted condition.

Figure 5:
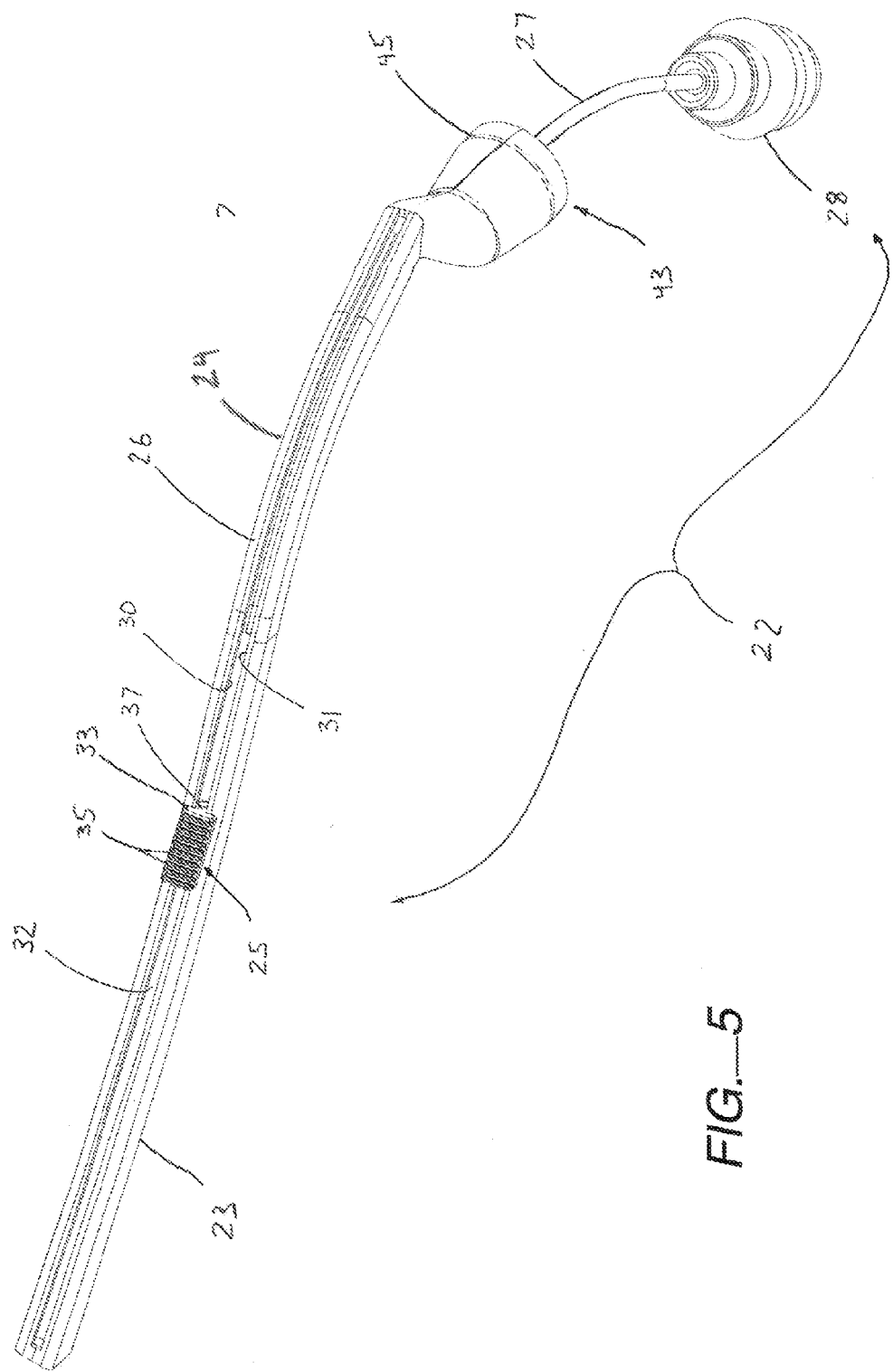
FIG. 5 is an enlarged, top perspective view of the temple arm of FIG. 4.

To slideable support the guide base 25 along the slot 32 of the guide track 26, as shown in FIGS. 5 and 8, the support wall 37 thereof slides between the opposed flanges 30, 31 of the guide track 26 that define the guide slot 32, while the lower mounting portion thereof slideably engages the passageway.

Briefly, it will be appreciated that while the guide track 26 and guide base 25 could be placed along the bottom or sides of the temple arm 23, the positioning atop the arm is preferred. For one, access to the upper tab portion 33 for operation thereof is easier. Moreover, positioning of the slot 32 at the top of the temple arm will eliminate entanglement, snaring or trapping of the tether in the slot, via gravity, during movement of the guide base.

The tether device 27 is preferably composed of a relatively flexible non-elastic material that provides sufficient tensile strength to secure the earplug device 28 thereto. Such tether flexibility is required to permit operational use of the earplug device 28 when the eyewear assembly 20 is being worn, and when the tether is oriented in the extended condition. Furthermore, the tether must be capable of conforming to the profile of the passageway 40 of the temple arm 23, along the fixed path, when the tether device 27 is moved to the retracted condition. Many cord or strap materials can be satisfactorily employed such as rope, twine, plastic, nylon, and other fabrics. One specific example of the tether material is a tether ribbon composed of fabric. While a non-elastic tether material is preferred, an elastic material can be employed, however.

It will be understood that the extension length of the tether device 27 can be controlled by the length of the fixed path from the first position toward the second position. For example, should the guide track 26 only extend from a proximal portion of the temple arm 23 to a central portion thereof (which incidentally is the orientation shown in FIGS. 4-6 and 8), the extension length of the tether device 27 from the retracted condition to the extended condition will be proportionately shortened. Thus, depending upon the application, the tether extension can be adjusted accordingly. Most preferably, however, the guide slot 32 extends nearly all the way to a distal end of the temple arm 23, providing as long a tether as possible, in the fully extended condition.

In accordance with the present invention, as the guide base 25 moves, slides and/or ratchets along the guide track 26, the tether is retained along the fixed path, substantially eliminating tether dangle. The guide track, in one specific embodiment, is provided by a rail-type structure (i.e., the relatively rigid guide base and guide track) that cooperates with the guide base 25 to move both the guide base and the one end of the tether along the fixed path. In one example, a ratchet type structure may be provided that locks the guide base along the fixed path between the first position and the second position unless the guide base, and hence the tether, is released. Other sliding-type devices suitable for use along the guided fixed path include plastic zippers and enclosed glide and pull devices.

In one specific configuration, the guide slot 32 defines a plurality of nubs or notches 42 spaced apart longitudinally along the slot 32 of the temple arm. These notches function to friction retain the guide base 25 selectively along the temple arm 23 for retainment of the earplug device, at selective extended conditions. The spaced notches 42 are preferably positioned along the top portion of the temple arm, adjacent to the guide slot 32. These notches 42 cooperate with the bottom surface of the upper tab portion 33, in a friction fit manner, to retain the guide base therealong until a manual sliding force, applied to the button portion, is sufficient to overcome the frictional retainment force between the notches 42 and the lower contact surface of the tab.

In one specific embodiment, the distal end of the temple arm 23 includes a parking structure 43 that is formed and dimensioned for at least partial receipt of the functional element (e.g., earplug device 28) therein when the guide base 25 is oriented in the first position, positioning the functional element in the parked condition (FIGS. 1 and 2). In this orientation, a proximal portion of the earplug device is retracted into the parking structure 43, functioning as a protective housing and storage assembly during non-use of the earplug.

As the guide base 25 is manually moved, via the upper tab portion 33, along fixed path of the guide track from the first position, where the tether device 27 is in the corresponding retracted condition (FIGS. 1 and 2), toward the second position, where the tether is moved toward the corresponding extended condition (FIGS. 4-7), the tether is therefore delivered from storage in the passageway 40 through the passageway distal opening 41.

Another technique to deliver the tether is by simply pulling on the earplug device 28, which in turn draws the tether through the passageway distal opening 41 to the retracted condition, and displaces the guide base 25 from the first position to the second position. This provides a sufficient extension or length of tether ribbon to enable mounting of the earplug device 28 to the user's ear.

During periods of non-use, the tether device 27 can be retracted back into the passageway 40 through the passageway distal opening 41. This is performed by manually manipulating the guide base 25, via the upper tab portion 33 along the guide track 26 from the second position (FIGS. 4-7) to the first position (FIGS. 1 and 2). The tether device 27 which is attached to the guide base 25 at the one end, is pulled and retracted back through the passageway distal opening 41 and along the fixed path of the passageway 40 toward the retracted condition.

As best shown in FIGS. 6 and 8, a distal edge portion 44 of the elongated body member 24 defines the opening 41 into a cavity 49 of the parking structure 43 sized and dimensioned for receipt of the functional element 28 therein. This cavity 49 is also communicates with the distal end of the longitudinal passageway 40, enabling reciprocal movement of the tether device 27 in and out of the parking structure 43. The parking structure further includes a distal funnel portion 45 wherein the corresponding portion of the passageway 40 funnels or flares outwardly. This tapered shape and inner diameter of the funnel portion 45 is configured for seated receipt of at least a proximal portion of the earplug assembly therein, by way of example, when the assembly is oriented in the retracted condition. This arrangement, thus, provides protection and storage of the earplug device when not in use.

The flare of the funnel portion 45 accommodates the larger diameter at the proximal portion of the earplug itself. It will be appreciated, however, that the largest diameter of the base of the earplug may be slightly larger than that of the parking structure, due to the compressible nature of most materials used for earplugs. Hence, such compression of the earplugs into the parking structure, when in the retracted condition, helps friction fit retain the earplug therein.

In another aspect of the present invention, detachable earplug assemblies are provided that can be easily attached and detached from the distal end of the tether devices. It will be appreciated that while virtually any earplug device may be mounted to the distal end of the tether device 27, preferably one that is detachable is beneficial. That is, by providing a means for detachable mounting of the earplug device to the distal end of the tether, more sanitary disposable earplug devices may be employed that can be simply and easily replaced and disposed thereof.

Referring now to FIGS. 9 and 10, one embodiment of a detachable earplug device 28 is shown having a conventional foam earplug member 51 that is molded around, and/or adhered to, a generally cylindrical-shaped, rigid, central post member 50. This elongated post member 50 is configured for positioning along a longitudinal axis of the earplug member 51, extending generally from a base proximal end of the earplug to a central portion thereof.

At the proximal end of the post member is a threaded screw member 52 formed for threaded mounting thereto. On a proximal side of the screw member 52 is an eyelet 53 that enables mounting to the tether device 27 or the like, while on a distal side of the screw member 52 is an opposed threaded end. This threaded end is configured for removable threaded mounting in a threaded passage formed in a proximal base portion 55 of the post member 50. This configuration enables removal and replacement of the earplug device 28 via the threaded screw member 52.

The central post member 50, therefore, rather than stiffening, primarily performs the function of providing a platform to mount the threaded screw member 52, as well as retaining the post member 50 to the foam earplug 51, via retaining disks 56 and 57. The post member, however, is relatively rigid in order to sufficiently accommodate the threaded coupling to the screw member 52. One particularly suitable material of the post member includes a thermo-elastic polymer material such as plastic or the like, although many other materials, including metal, can be employed. This is beneficial in that the post member 50 is significantly more rugged and easily moldable.

Referring now to FIGS. 11-16, alternative embodiment temple arms 23, 23' for eyewear assembly 20 are shown which are configured to support respective functional elements, such as a clips, can openers or earplugs 28, 28'. The temple arms 23, 23' each including an elongated body member 24, 24' having a proximal portion configured to mount to the eyewear device 21, and an opposite distal portion thereof defining a parking structure 43, 43'. As best shown in FIGS. 15 and 16, each parking structure includes a distal opening 41 into a substantially enclosed cavity 49 thereof. Each temple arm further includes a respective elongated flexible tether 27 having a distal portion thereof mounted to the functional element 28, and slideably extending through the parking structure cavity for movement of functional element between the parked condition and the operational condition. In the parked condition, the functional element is slideably parked at least partially within the cavity 49. In the operational condition, the function element 28 is positioned sufficiently out of the parking structure to enable operation thereof. In accordance with the present invention, the this aspect of the temple arm 23 includes a cover member 100 configured to cooperate with the parking structure 43 for movement between an opened condition (FIGS. 13, 15 and 16) and a closed condition (FIGS. 11, 12 and 14). In the opened condition, the functional element 28 can be moved back and forth between the stored condition (FIG. 15) and the operational condition (FIG. 16). In the closed condition, the cover member 100 extends over the parking structure opening 41, wherein the parking structure 43 and the cover member 100 cooperate to substantially enclose the functional element therein.

Accordingly, a protective cover member is provided that is capable of moving from the opened condition (FIGS. 13, 15 and 16) to a protective closed condition (FIGS. 11, 12 and 14). As mentioned, in this closed condition, the functional element is jointly encased between the parking structure and the cover member for protection, maintaining the cleanliness of the functional element as well as preventing in advertent snagging thereof when not in use.

Henceforth, only one cover member 100 and the corresponding temple arm will be described in detail for clarity. Briefly, it will be appreciated that this embodiment of the present invention also includes the flexible tether device 27, slideable support mechanism 25, guide base 25 and guide track 26 of the previous embodiments described above.

Turning now to FIGS. 19-22, the cover member 100 may be any exterior shape, although it should be sized and dimensioned to that cooperate with the distal edge portion 44 for enclosing the cavity 49. Accordingly, while a dome-shaped shell is shown for the cover member, many other shapes may be employed. The dome-shaped cover member 100, however, is aesthetically pleasing, integrating nicely and flush with the distal funnel portion 45 of the parking structure, as well as naturally providing a interior dome shape to accommodate the distal portion of one particular functional element 28 (i.e., an earplug).

In one embodiment, as just mentioned, the functional element 28 is in the form of an earplug device, wherein only the proximal and mid-portion thereof are received in the cavity 49. The remaining distal portion of the earplug device 28 is received in the dome shaped cover member (as shown in FIG. 15).

The cover member 100 is preferably hingeably mounted to the distal funnel portion 45, via a hinge device 101. This enables the cover member 100 to rotate about a rotational axis of the hinge between a closed position (FIGS. 11, 12 and 14), covering and protecting the earplug device 28, and an opened position ((FIGS. 13, 15 and 16), enabling operational access to the earplug device 28.

In one configuration, the hinge device 101 is disposed on the outside of the cavity 49, between distal funnel portion 45 and the cover member 100. FIGS. 12, 14, 17, and 23 best illustrate that the hinge device 101 includes a pair of spaced-apart hinge knuckles 102, 103 extending upward from an upper exterior surface of the distal funnel portion 45 of the parking structure. Each knuckle 102, 103 includes a horizontally oriented knuckle eyelet 105, 106 axially aligned with one another.

As shown in FIG. 14, the cover member 100 includes a support rib 107 extending longitudinally along the top thereof. A proximal portion of the support rib 107 is sized and dimensioned for positioning for sliding, rotational receipt between the spaced knuckles 102, 103 of the parking structure 43. The proximal portion 108 of the support rib 107 further includes a horizontally extending rib eyelet (not shown) that is oriented to axially align with the knuckle eyelets 105, 106.

Once the rib eyelet and the knuckle eyelets 105, 106 are axially aligned, a pin or screw 111 can be inserted that enables hinged rotation of the cover member thereabout between the opened (generally about 90°) and closed conditions.

A spring device (not shown) may cooperate with the hinge device 101 to bias the cover member 100 toward either the opened condition, the closed condition or both. When biased toward the opened condition, the cover member 100 can be maintained in the opened condition to facilitate access to the ear plug device 28. Manual force may then be necessary to overcome the spring force, and move the cover toward the closed condition. Similarly, should the cover member 100 be biased toward the closed condition, the cover device can be maintained in the closed condition until the necessary manual force is applied to overcome the spring force, opening the cover member 100.

While the hinge device 101 is shown in an orientation above the parking structure, it will be appreciated that this hinge device may be positioned anywhere radially around the distal edge portion 44 of the opening into the cavity 49. Moreover, the hinge positioning can be interiorly mounted so that it is generally contained within the cavity 49 and the dome-shaped shell.

Moreover, it will be understood that the cover member 100 may be removably mounted to the distal funnel portion 45 using numerous conventional techniques such as by snap-fit techniques, latches, threaded techniques, etc.

To facilitate gripping of the cover member 100 during opening of the cover from the closed position, a pair of opposing grip recesses 112, 113 are defined at the sides of the distal funnel portion 45 of the parking structure 43. When the cover member is in the closed condition, the grip recesses 112, 113 enhance exposure of the corresponding edge portions of the domed cover member 100. This easily allows access to the edges by the operator fingertips.

In one specific embodiment, to further facilitate maintenance of the cover device in the closed condition, the assembly may incorporate a snap-fit latch system 115. As best shown in FIGS. 15 and 16, a simple integral latch 116 can be provided having a biased tab portion 117 that is received within a corresponding hole or receptacle 118 formed and aligned in the cover member 100. Other latch systems can include magnetic based latches, hooks, etc.

Although the present invention has been described in connection with the preferred form of practicing it and modifications thereto, those of ordinary skill in the art will understand that many other modifications can be made thereto within the scope of the claims that follow. Accordingly, it is not intended that the scope of the invention in any way be limited by the above description, but instead be determined entirely by reference to the claims that follow.

What is claimed is:

1. An eyewear temple arm apparatus for an eyewear device, and configured to support an earplug having a proximal portion and a distal portion, said temple arm apparatus comprising:
    an elongated body member having a proximal portion configured to mount to the eyewear device, and an opposite distal portion thereof defining a parking structure having a distal edge portion that defines an opening into a cavity thereof, said cavity being formed and dimensioned for free sliding, peripheral receipt of at least said proximal portion of the earplug therein between an operational condition and a parked condition;
    a cover member configured to cooperate with said parking structure for movement between an opened condition, enabling the earplug therein to move to said operational condition, and a closed condition, extending over the parking structure opening to substantially enclose at least said distal portion of the earplug therein;
    an elongated flexible tether having a distal portion thereof mounted to the earplug, and slideably extending through the parking structure cavity; and
    a guide base slideably cooperating with said elongated body member for movement between a first position and a second position;
    wherein said elongated body member defines a passageway extending longitudinally therethrough and distally terminating at the parking structure cavity, said passageway being sized and dimensioned for reciprocal sliding receipt of said tether therein as the guide base is moved between the first position and the second position.

2. The eyewear temple arm apparatus according to claim 1, wherein
    said cover member hingeable moves between the opened condition and the closed condition.

3. The eyewear temple arm apparatus according to claim 2, further including:
    a hinge device hingeably mounting the cover member to the parking structure.

4. The eyewear temple arm apparatus according to claim 1, wherein
    said cover member is a generally dome-shaped shell.

5. An eyewear assembly comprising:
    an eyewear device;
    a pair of temple arms each having
        an elongated body member having a respective proximal portion thereof mounted at opposed sides of the eyewear device, and an opposite distal portion thereof defining a respective parking structure with an opening into a substantially enclosed cavity thereof, each said cavity being formed and dimensioned for free sliding, peripheral receipt of at least a proximal portion of a respective functional element therein between an operational condition and a parked condition,
        a cover member configured to cooperate with said parking structure for movement between an opened condition, enabling the respective functional element therein to move to said operational condition, and a closed condition, extending over the parking structure opening to substantially enclose at least said distal portion of the respective functional element therein;
        an elongated flexible tether having a distal portion thereof mounted to the earplug, and slideably extending through the parking structure cavity; and
        a guide base slideably cooperating with said elongated body member for movement between a first position and a second position;
    wherein each said elongated body member defines a passageway extending longitudinally therethrough and distally terminating at the parking structure cavity, said passageway being sized and dimensioned for reciprocal sliding receipt of said tether therein as the guide base is moved between the first position and the second position.

6. The eyewear assembly according to claim 5, wherein
    each said cover member hingeable moves between the opened condition and the closed condition.

7. The eyewear assembly according to claim 5, wherein
    each said parking structure is generally conical-shaped, and
    each said cover member is a generally dome-shaped shell.

8. The eyewear assembly according to claim 5, wherein
    each said functional element is an ear device earplug.

9. The eyewear assembly according to claim 8, wherein
    said ear device is an earplug.

10. An eyewear temple arm apparatus for an eyewear device comprising:
    a functional element having a proximal portion and a distal portion;
    an elongated body member having a proximal portion configured to mount to the eyewear device, and an opposite distal portion thereof defining a parking structure having an opening into a substantially enclosed cavity thereof;
    an elongated flexible tether having a distal portion thereof mounted to the functional element, and slideably extending through the parking structure cavity for movement of functional element between a parked condition, slideably parking the functional element at least partially within said cavity, and an operational condition, positioning the functional element sufficiently out of the parking structure to enable operation thereof;
    a cover member configured to cooperate with said parking structure for movement between an opened condition, enabling the functional element therein to move to said operational condition, and a closed condition, extending over the parking structure opening wherein said parking structure and said cover member cooperate to substantially enclose the functional element;
    a guide base slideably cooperating with said elongated body member for movement between a first position and a second position;
    an elongated flexible tether having a proximal end mounted to the guide base and a distal portion thereof mounted to the functional element;
    wherein said elongated body member defines a passageway extending longitudinally therethrough and distally terminating at the parking structure cavity, said passageway being sized and dimensioned for reciprocal sliding receipt of said tether therein as the guide base is moved between the first position and the second position.

11. The eyewear temple arm apparatus according to claim 10, wherein
said cover member is hingeably coupled to the parking structure for movement between the opened condition and the closed condition.

12. The eyewear temple arm apparatus according to claim 10, wherein
said cover member is a generally dome-shaped shell.

13. The eyewear temple arm apparatus according to claim 10, wherein
said elongated body member further defines an elongated slot extending adjacent to, and in communication with, said passageway, said slot being formed and dimensioned for sliding support of said guide base therealong between the first position and the second position.

14. The eyewear temple arm apparatus according to claim 10, wherein
said functional element is an ear device.

15. The eyewear temple arm apparatus according to claim 14, wherein
said ear device is an earplug.

* * * * *